(12) United States Patent
Wong et al.

(10) Patent No.: US 9,404,800 B2
(45) Date of Patent: Aug. 2, 2016

(54) WAVELENGTH-ENCODED TOMOGRAPHY

(71) Applicant: THE UNIVERSITY OF HONG KONG, Hong Kong (CN)

(72) Inventors: Kenneth Kin Yip Wong, Hong Kong (CN); Chi Zhang, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 110 days.

(21) Appl. No.: 14/511,570

(22) Filed: Oct. 10, 2014

(65) Prior Publication Data

US 2015/0168214 A1    Jun. 18, 2015

Related U.S. Application Data

(60) Provisional application No. 61/890,048, filed on Oct. 11, 2013.

(51) Int. Cl.
*G01J 3/46* (2006.01)
*G01J 3/28* (2006.01)
*G01B 9/02* (2006.01)

(52) U.S. Cl.
CPC ............... *G01J 3/28* (2013.01); *G01B 9/02004* (2013.01); *G01B 9/02044* (2013.01); *G01B 9/02091* (2013.01); *G01B 9/02097* (2013.01)

(58) Field of Classification Search
CPC .................. G01B 9/02004; G01B 9/02097
See application file for complete search history.

(56) References Cited

U.S. PATENT DOCUMENTS 7,903,705 B2 *   3/2011   Apolonski ............ H01S 3/1112
                                                        372/25
8,514,898 B1 *   8/2013   Pang ....................... H01S 3/105
                                                        372/100

OTHER PUBLICATIONS

Keisuke Goda, "Theory of amplified dispersive Fourier transformation", Physical Review 2009.*
Benjamin Potsaid, "Ultrahigh speed 1050nm swept source /Fourier domain OCT retinal and anterior segment imaging at 100,000 to 400,000 axial scans per second" Optics Express Sep. 13, 2010.*

* cited by examiner

*Primary Examiner* — Michael A Lyons
*Assistant Examiner* — Maurice Smith
(74) *Attorney, Agent, or Firm* — Saliwanchik, Lloyd & Eisenschenk (57) ABSTRACT

Systems and methods for non-invasive optical imaging are provided. One or more time-lenses can be utilized to perform an optical Fourier transform, and the time-to-wavelength conversion can generate a wavelength-encoded image of optical scattering, analogous to optical coherence tomography. This optical Fourier transform provides improved axial resolution and simplifies digital signal processing after data acquisition.

14 Claims, 6 Drawing Sheets

WAVELENGTH-ENCODED TOMOGRAPHY

CROSS-REFERENCE TO RELATED APPLICATION

This application claims the benefit of U.S. provisional application Ser. No. 61/890,048, filed Oct. 11, 2013, which is herein incorporated by reference in its entirety.

BACKGROUND OF THE INVENTION

Medical imaging can include capturing images of biological structures by using, for example, Computer Aided Tomographic (CAT) scanning, and can be a highly beneficial biophotonic measuring technique. A biophotonic system, which may be useful for, e.g., cardiovascular medical applications may comprise a tomographic imaging device and one or more endoscopic instruments. Biophotonic applications may also include dermatological (e.g., skin tissue) examinations and/or imaging of dental structures.

Tomographic imaging technologies, such as the computed tomography by x-ray, magnetic resonance imaging (MRI), ultrasound imaging, and optical coherence tomography (OCT) have found widespread applications in micro-scale bio-medical imaging. Among these technologies, OCT is advantageous in terms of resolution, owing to its short wavelength. Optical frequencies are beyond the detectable range of electrical means, and OCT systems leverage the low frequency introduced by an interferometer to differentiate reflective depth. In addition, some straightforward methods like radio detection and ranging (RADAR) or optical time domain reflectometers (OTDR) can only measure large-scale distances, and the resolution is limited by the bandwidth of the oscilloscope.

OCT has proven to be useful in medical and laboratory environments at least in part due to a capability for resolving fine structures in a non-invasive manner. OCT may be useful, for example, in performing optical biopsies, which can permit a physician or other medical professional to perform noninvasive in vivo imaging without a need for slicing tissue samples. OCT can also allow for imaging of highly scattered biological tissues with a high resolution.

BRIEF SUMMARY OF THE INVENTION

Embodiments of the subject invention provide advantageous systems and methods for non-invasive optical imaging (e.g., non-invasive, optical, cross-sectional imaging), which have a wide range of uses and are particularly beneficial in biological systems. A wavelength-encoded tomography system can utilize one or more time-lenses to perform an optical Fourier transform, and the time-to-wavelength conversion can generate a wavelength-encoded image of optical scattering from internal microstructures (e.g., analogous to interferometery-based imaging such as optical coherence tomography). Optical Fourier transform, provides better axial resolution than electrical Fourier transform and greatly simplifies the digital signal processing after data acquisition.

In an embodiment, an imaging system can include: a sample platform; a photodetector; a linear frequency-shifted device positioned such that light from the sample passes through the linear frequency-shifted device before it reaches the photodetector; and a processing device in operable communication with the photodetector and configured to receive an output spectrum from the photodetector and realize a spatial-to-wavelength conversion, of the output spectrum, solely in the optical domain. The linear frequency-shifted device can include one or more time-lenses. The system can be capable of achieving an imaging resolution of 150 µm or less with a spectral width of 7.5 nm, and an A-scan rate of at least 100 MHz.

In another embodiment, a method for imaging a sample can include: placing the sample on a sample platform of an imaging system; positioning a linear frequency-shifted device such that light from the sample passes through the linear frequency-shifted device before it reaches a photodetector of the imaging system; receiving, by a processing device in operable communication with the photodetector, an output spectrum from the photodetector; and realizing, by the processing device, a spatial-to-wavelength conversion, of the output spectrum, solely in the optical domain. The linear frequency-shifted device can include one or more time-lenses. The method can achieve an imaging resolution of 150 µm or less with a spectral width of 7.5 nm, and an A-scan rate of at least 100 MHz.

DETAILED DISCLOSURE OF THE INVENTION

Embodiments of the subject invention provide advantageous systems and methods for non-invasive optical imaging (e.g., non-invasive, optical, cross-sectional imaging), which have a wide range of uses and are particularly beneficial in biological systems. A wavelength-encoded tomography system can utilize one or more time-lenses to perform an optical Fourier transform, and the time-to-wavelength conversion can generate a wavelength-encoded image of optical scattering from internal microstructures (e.g., analogous to interferometery-based imaging such as optical coherence tomography). Optical Fourier transform, provides better axial resolution than electrical Fourier transform and greatly simplifies digital signal processing after data acquisition.

In an embodiment, an optical imaging system can capture tomographic (layer) images in a non-invasive manner and enable ultrafast frame rate with high resolution and sensitivity. The system can include one or more of the following elements: means for introducing a linear frequency shifted device (e.g., a time-lens) in front of a sample being imaged (e.g., between the sample platform and a photodetector of the system); means for differentiating the depth induced delay when the light transmits forward and backward through the system, as the spectrum is stretched and compressed; means for illuminating light on the sample by a swept-source, as different reflecting depth results in different output wavelengths after the compression process, thereby realizing the identification of different layers; and means (e.g., a processing device such as a processor of a computing device, or an optical spectrum analyzer) for realizing the spatial to wavelength conversion all in the optical domain without pursuing mandatory electrical Fourier transformation (as in OCT). All components can be in operable communication with each other (e.g., via wires, wirelessly, or a combination of both). The system can be configured for: realizing the all-optical spatial to wavelength conversion, with flexible conversion factor for different applications; providing orders of magnitude improvement on the frame rate, as high as megahertz or even gigahertz, compared with the related art OCT systems; or both.

Existing tomographic imaging technologies have limitations with regard to resolution, depth, and frequency. To help address these limitations, an ultrafast optical oscilloscope incorporating a time-lens approach can be used. A short pulse of 200 femtoseconds (fs) can be resolved in the spectral domain. The combination of two schemes (OTDR and the time-lens oscilloscope) can directly convert a tiny depth difference into a wavelength shift, thereby providing an advantageous solution for advanced ultrafast tomographic applications; such a solution is referred to herein as wavelength-encoded tomography (WET). This technique overcomes inherent speed limitation of OCT, while also improving the resolution in non-invasive cross-sectional imaging.

Figure 1:
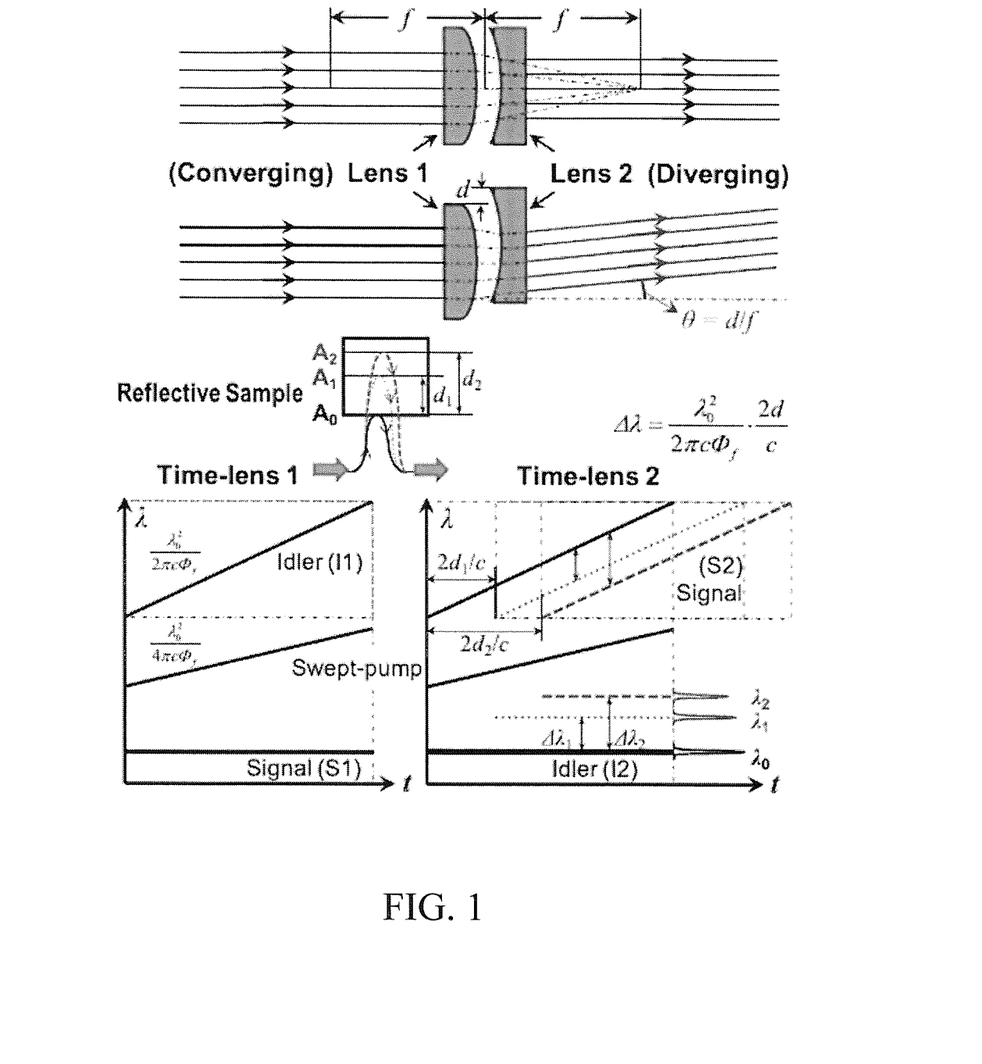
FIG. 1 shows a schematic of the principle of depth-to-wavelength conversion in the spatial domain by a system according to an embodiment of the subject invention.

It is possible that the femtosecond pulse used by the time-lens oscilloscope may encounter undesirable nonlinear effects in biological samples, which would affect the imaging quality of a linear scattering system (e.g., OCT). Therefore, in many embodiments of the subject invention, the single time-lens focusing structure can be adjusted to two time-lenses, with opposite focal group-dispersion delays (GDDs) to avoid the ultra-short pulse interacting with the sample. FIG. 1 shows a temporal ray diagram of a WET configuration according to an embodiment, which can be understood by the space-time duality.

Referring to FIG. 1, the spatial distance (d) along the vertical axis corresponds to the temporal delay ($\Delta t$), and the spatial axial angle ($\theta$) corresponds to the temporal wavelength ($\Delta \lambda$). In the uppermost portion of FIG. 1, one converging lens and one diverging lens with identical focal lengths (f) are aligned with each other, and tilting of the axial angle ($\theta$=d/f) is achieved by the offset (d) between these two lenses along the vertical axis (the portion just below in FIG. 1, to where the lower arrows from the labels "Lens 1" and "Lens 2" are pointing). Therefore, in the temporal domain, these two corresponding time-lenses can realize linear optical mapping between the reflective temporal delay ($\Delta t$=2d/c) and the wavelength ($\Delta \lambda$). In addition, no short pulse is involved throughout this process, and the energy is distributed uniformly along the time span.

In an embodiment, two time-lenses are implemented with a swept-pumped four-wave mixing (FWM) process (the plots in the lower portion of FIG. 1), owing to the required large swept bandwidth and less than gigahertz frame rate. The identical focal GDDs ($\Phi_f$) are achieved with the same swept-pump, while the converging and diverging features are realized with different parametric mixing directions, from short wavelength to long wavelength and vice versa. After time-lens 1, the newly generated idler can be launched to illuminate a reflective sample, which can scatter the idler along the temporal axis before combining together with the same swept-pump in time-lens 2. In certain embodiments, time-lens 2 generates a quasi-CW (where CW refers to continuous wave) source as the input signal, and the delayed idler changes its wavelength, represented by the dashed and dotted lines shown in the plot at the lower right-hand side of FIG. 1. This mechanism provides a linear relation between the reflection depth (d) and the output wavelength shift ($\Delta \lambda$) as follows:

$$\Delta \lambda = \frac{\lambda_0^2}{2\pi c} \cdot \frac{\Delta t}{\Phi_f} = \frac{4}{cDL} d = \varepsilon \cdot d, \quad (1)$$

where c is the speed of light, DL is the swept-pump dispersion (which can be generated from, e.g., a stretched pulse), and $\epsilon$=4/cDL is the depth-to-wavelength ratio. The detailed derivation of $\epsilon$ can be obtained from the plot at the lower right-hand side of FIG. 1 and Zhang et al. (Appl. Opt. 52, 8817-8826, 2013), which is hereby incorporated herein by reference in its entirety.

Figure 2:
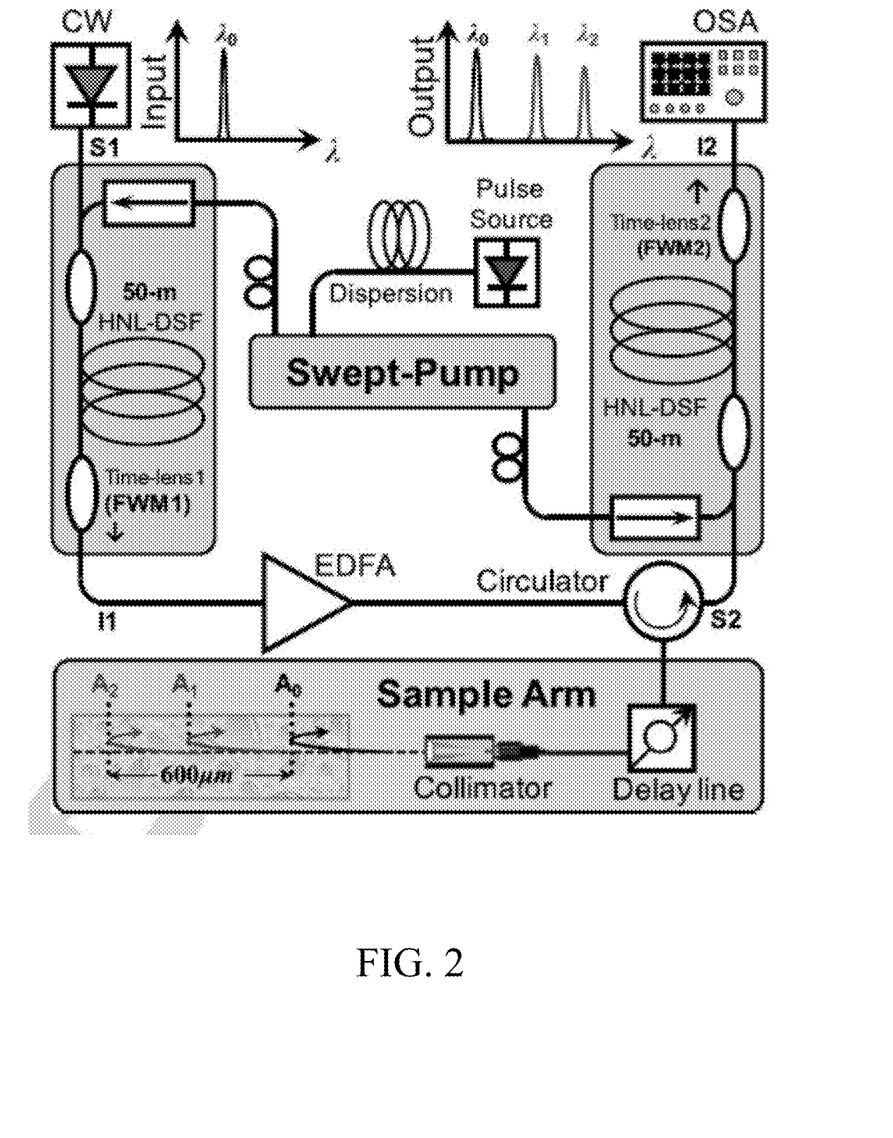
FIG. 2 shows a schematic of an imaging system according to an embodiment of the subject invention.
Figure 3A:
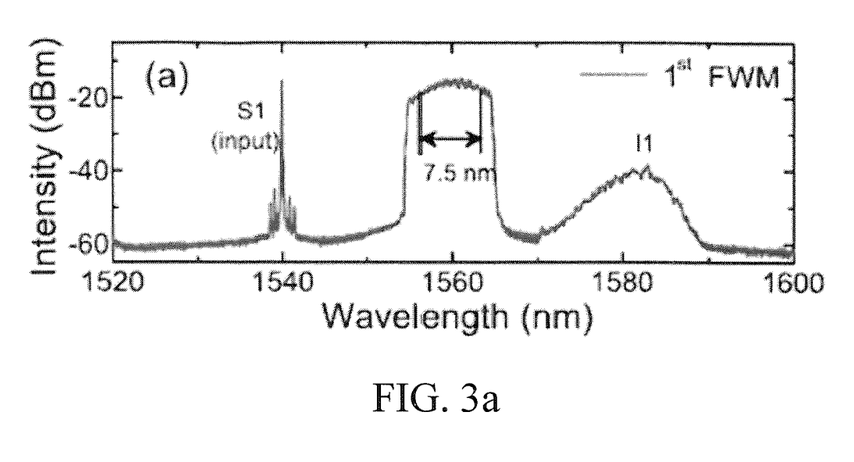
FIG. 3(a) shows a spectrum of mixing in a system according to an embodiment of the subject invention.

FIG. 2 shows a schematic of an imaging apparatus according to an embodiment of the subject invention. Though certain values are shown in FIG. 2, these are for exemplary purposes only and should not be construed as limiting. Referring to FIG. 2, a setup including two time-lenses is shown. A pulsed source (e.g., 500-fs pulsewidth, $\lambda_{BW}$=7.5 nm) can pass through a spool of fiber (e.g., 1-km single-mode fiber, such as SMF-28, DL=17 picoseconds/nanometer (ps/nm)) to generate the swept-pump for the two-stage FWMs. The FWM can leverage the third-order nonlinear susceptibility $\chi$ in two spools of fibers (e.g., 50-m highly-nonlinear dispersion-shifted fibers (HNL-DSFs)). The zero-dispersion wavelength can be at, for example, 1554 nm, though embodiments are not limited thereto. In the first-stage FWM (the left shaded box in FIG. 2), a signal S1 (e.g., a 1-mW CW signal) and the swept-pump (which can be amplified, e.g., to 100 milliWatts (mW)) generate the idler (I1) with doubled swept range. The doubled swept range is shown in FIG. 3(a). The idler (I1) can have a value of, e.g., 0.5 mW, though embodiments are not limited thereto. The idler (I1) can be filtered out by a wavelength-division multiplexing (WDM) filter and amplified (e.g., to 10 times its initial value such as to 5 mW) by an amplifier before illuminating the sample. In a particular embodiment, the amplifier can be an L-band Erbium doped fiber amplifier (EDFA).

Figure 3B:
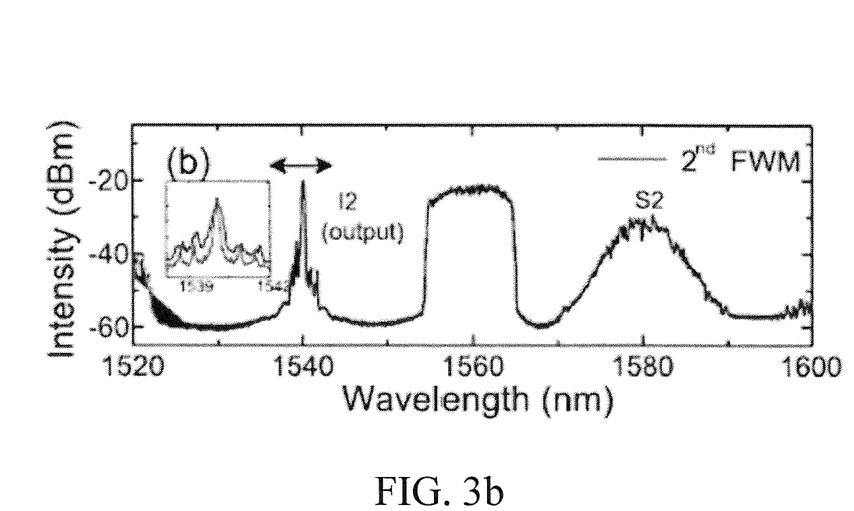
FIG. 3(b) shows a spectrum of mixing in a system according to an embodiment of the subject invention.

The sample arm (or sample platform) can introduce some loss (e.g., ~10-dB loss), and different reflection depths can scatter the idler (I1) with corresponding temporal delays. An optical delay line in the sample arm can synchronizes the scattered idlers (S2, as the signal for the second-stage FWM) with the second swept-pump. Therefore, after the second-stage FWM, the idler (I2) is generated at the original signal wavelength, and this is depicted in FIG. 3(b). The idler (I2) can have a value of, e.g., ~0.2 mW, though embodiments are not limited thereto. The idler (I2) spectrum can be captured by a processing device, such as an optical spectrum analyzer (for example, OSA, Yokogawa AQ6370C, 0.05-nm resolution) and can manifest the spatial information ($A_0$, $A_1$, and $A_2$ in the sample arm of FIG. 2). The spatial information is shown as the output spectra ($\lambda_0$, $\lambda_1$, and $\lambda_2$) of FIG. 2. Moreover, the two time-lenses configuration can employ a CW source as the signal, and in this case no synchronization is required between the signal and pulsed pump, unlike related art imaging devices. The overall setup can be pictorially viewed as a "lock" system: the FWM1 can lock a swept-pump onto the CW signal, and the FWM2 using the same swept-pump as a "key" to unlock the temporal delay (i.e., reflection depth information) from the wavelength shifting.

According to Equation (1), the output wavelength shift ($\Delta \lambda$) is directly proportional to the reflection depth (d). To quantitatively characterize this feature, a precision translation stage can be introduced to control the reflective mirror. In the WET system according to certain embodiments of the subject invention, the spatial resolution ($R_{WET}$) refers to the capability of an optical imaging system to distinguish different layers, which can be calculated with the spectral width ($\delta\lambda$) and the mapping ratio ($\epsilon$). The ideal $\delta\lambda$ can be determined by the temporal pulsewidth ($\lambda_{BW}DL$), which can be narrowed by the FWM process. Frequency intensity fluctuation of the swept-pump may limit $\delta\lambda$. If there is no intensity fluctuation over the envelope of the swept-pump, and phase-matching condition is satisfied over the whole conversion range, then the spatial resolution of the WET system can be shown as $$R_{WET} = \delta\lambda/\epsilon = \lambda_0^2/(2\pi c) \times 4 \ln 2/(\lambda_{BW}DL) \times cDL/4 = \ln 2\lambda_0^2/(2\pi\lambda_{BW}), \quad (2)$$

where $\lambda_{BW}$ is the full-width at half-maximum (FWHM) of the swept-pump spectrum. Based on the pump bandwidth ($\lambda_{BW}$), the ideal spatial resolution can be calculated. Compared with OCT, system of the subject invention can achieve four times sharper resolution with the same bandwidth ($\lambda_{BW}$) based on Equation (2). The doubled frequency relation from the swept-pump to the idler in the FWM (i.e., the idler bandwidth can be doubled of the pump) contributes a factor of two, and the optical Fourier transform (i.e., WET) achieves better temporal resolution over the digital (electrical) Fourier transform (i.e., OCT) by another factor of two. Specifically, the optical Fourier transform by the time-lens has taken into account the phase term, while the electrical Fourier transform in OCT is performed after the square-law photodetector, which only considers the intensity part. The second factor of two is guaranteed, while the first factor (conversion bandwidth) could potentially be limited in certain circumstances by the phase-matching condition of the FWM.

FIGS. 3(a) and 3(b) show the spectra of two-stage FWMs. The conversion bandwidth can also limit the resolution in certain circumstances, and the phase matching condition can require shorter HNL-DSF with lower dispersion coefficient (D) and slope (S). Some advanced dispersion-engineered nonlinear medium, such as a silicon waveguide, can help to achieve 100-nm FWM wavelength conversion bandwidth, which can benefit the implementation of a WET system according to embodiments of the subject invention. The inset of FIG. 3(b) shows a comparison between the input and the output spectra, which is broadened. Two factors can contribute to this spectral broadening effect: the phase-mismatching can decrease the pulsewidth of idler (I1) by 30%, since its bandwidth is degraded after FWM1 (as shown in FIG. 3(a)); and the temporal intensity fluctuation of the swept-pump can introduce another factor of two to the spectral width of the idler (I2). Considering the same narrowing effect in FWM2, the pulsewidth of idler (I2) can decrease by half, thereby broadening the spectral width by a factor of two.

Figure 5:
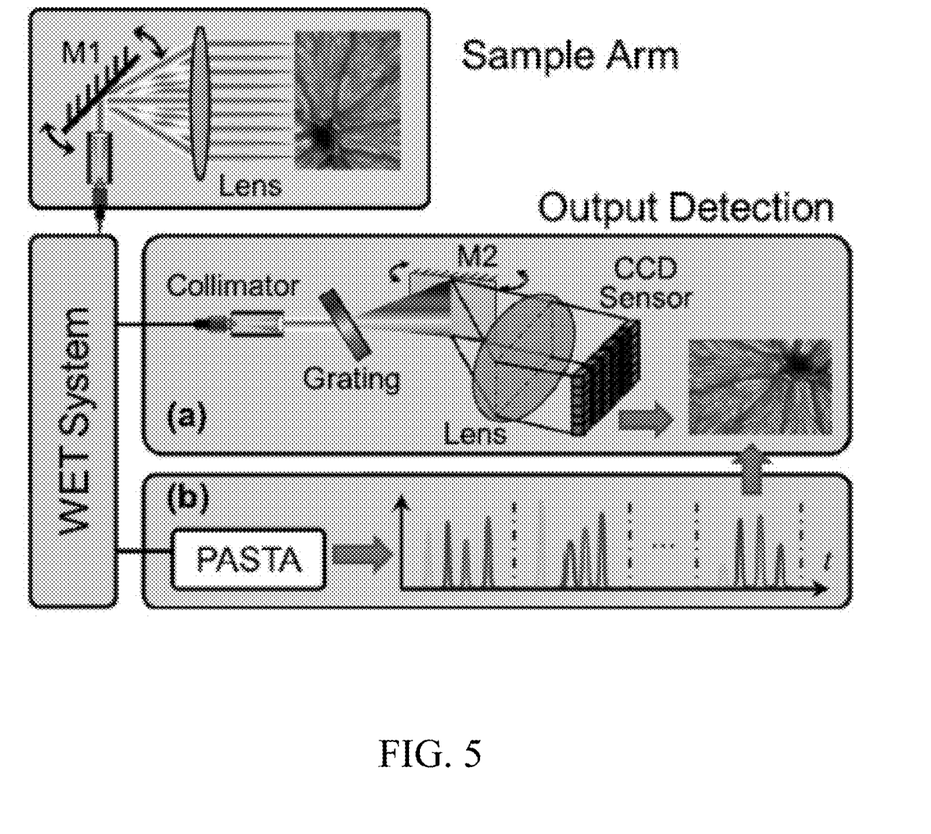
FIG. 5 shows a schematic of an imaging system according to an embodiment of the subject invention.

FIG. 5 shows an imaging apparatus according to an embodiment of the subject invention. To capture a 2D cross-sectional image, a galvo mirror (M1) can be used to scan in the sample arm as shown in the top box of FIG. 5. The apparatus having two time-lenses can optically convert the depth information to spectrum, and the spectrum can be captured to construct the 2D image. In this sense, it is similar to spectral-domain OCT (SD-OCT), which also requires a spectrometer to capture the spectral information. However, the spectrum in SD-OCT carries interference fringes, and further Fourier transform is required to retrieve the depth information. In a WET system/apparatus according to the subject invention, the spectrum can directly generate the depth information (with better resolution compared to SD-OCT), for example, by being captured by a synchronized single-shot spectrometer. The system can therefore be configured as an ultrafast tomographic system.

To fully utilize the high frame rate (e.g., 100-MHz frame rate) of the systems of the subject invention, two methods can be used. In one such method, the spectrum can be dispersed onto a spatial CCD sensor (FIG. 5(a)) and another scanning galvo mirror (M2) can be combined along the horizontal direction to construct the 2D image. Mirrors M1 and M2 can be synchronized by the identical driving signal, and the B-scan rate can be determined by the frame rate of the CCD sensor (as high as ~kHz). In another such method, an ultrafast optical spectrum analyzer can be utilized—a parametric spectro-temporal analyzer (PASTA), with high resolution (e.g., 0.02-nm resolution). The PASTA system can share the same pump source with the WET system, which naturally synchronizes these two systems together, therefore fully utilizing the 100-MHz A-scan rate, as shown in FIG. 5(b).

A time domain OCT (TD-OCT) approach is sometimes employed for rapid image capture. TD-OCT can include a Michelson-type interferometer and focused sample arm beam arranged in a lateral-scanning mechanism. Another approach toward improving noninvasive medical imaging can include "single-shot" imaging, in which a large amount of imaging measurements can be performed in a very short period of time. Single-shot imaging can benefit from enhanced OCT imaging speed which may achieved at least in part through use of, for example, frequency domain optical coherence tomography (FD-OCT). In FD-OCT, axial (e.g., axial line, A-line, etc.) back-reflection signals in a frequency domain can be exploited, which can equate to, for example, a wave-number domain.

In embodiments of the subject invention, WET can provide advantages over TD-OCT and FT-OCT. For example, embodiments can reduce or eliminate a need for a reference branch, which may be used to bring about, for example, an interference pattern between direct and scattered imaging beams generated in OCT systems. Thus, if a reference branch is not utilized (i.e., excluded), optical components that may introduce data capture speed limitations, such as a Mach Zehnder interferometer for capturing phase shifts at locations within an interference pattern, may be eliminated. Additionally, an all-optical process can be used, in which the output signal intensity from optical components directly reflects the spatial information. Accordingly, in certain embodiments, post processing, which can sometimes be performed after optical signals are converted to electrical signals, need not be performed. At least as a partial consequence of eliminating or reducing the need for electronic post processing, a WET system may bring about considerable, (e.g., a tenfold or more) increase in frame rate. Improvements can enable capture of as many as, e.g., 1,000,000 or 1,000,000,000 frames per second, though embodiments are not limited thereto. An additional benefit can be a reduction in system complexity over TD-OCT and/or FD-OCT approaches.

Referring again to the plots in the lower portion of FIG. 1, in an embodiment, a WET system can leverage time-sensitive features of a linear frequency shifting device (time-lens) to differentiate spatial depth induced delay. A principal portion of a WET system can include a spatial depth-to-wavelength conversion. A two-stage, four-wave mixing (FWM1) element can be employed. A first stage can use a swept-pump ("lock") signal and a CW signal to generate optical signals corresponding to a double-chirped idler to illuminate a sample undergoing imaging. In embodiments, responsive to illumination, different layers of a sample undergoing imaging may scatter or reflect an idler signal at different times. Scattered idlers may be combined with the same swept-pump signal ("unlock") in a second stage FWM2, spatial information. A sample undergoing imaging can reflect idler signals at different times, based at least in part on distances of scattering layers, such as, for example, $d_1$ and $d_2$. Reflected or scattered optical signals incident at FWM2 can be converted to wavelength information.

Referring again to the upper portion of FIG. 1, a corresponding temporal ray diagram is shown, where a two-stage FWM can be treated as a pair of converging and diverging time-lenses having identical focal length. The temporal ray diagrams show the WET principle, based on the space-time duality. When a converging lens is synchronized with the diverging lens, as shown in the uppermost portion of FIG. 1, an output beam may continue to be along the same direction. If there is a temporal mismatch ($\Delta t_d$) between the converging lens and the diverging lens, as shown in FIG. 1 (the portion to where the lower arrows from the labels "Lens 1" and "Lens 2" are pointing), an output beam may be redirected along a certain axial angle, which may comprise a different output wavelength.

In accordance with the principle of the space-time duality, the axial angle (or exit angle) may refer to the wavelength and the vertical direction refers to the time axis. Thus, spatial depth induced time delay ($\Delta t_d$) may result in vertical movement of the second time-lens, and may further convert a parallel beam comprising exit angle ($\theta = \Delta t_d / \phi_f$), that is, a different wavelength in this temporal ray diagram. This mechanism can provides a linear relation between the reflection depth (d), such as $d_1$ and $d_2$ shown in the plots in the lower portion of FIG. 1, and the output wavelength shift ($\Delta \lambda$), which can be expressed as follows:

$$\Delta \lambda = \frac{4d}{cDL}, \quad (3)$$

where c is the speed of light, D is the swept pump dispersion, and L is the dispersive fiber length. From Equation (3), it can be seen that the mapping ratio between depth and wavelength can be easily adjusted by controlling the pump dispersion (D).

Figure 6:
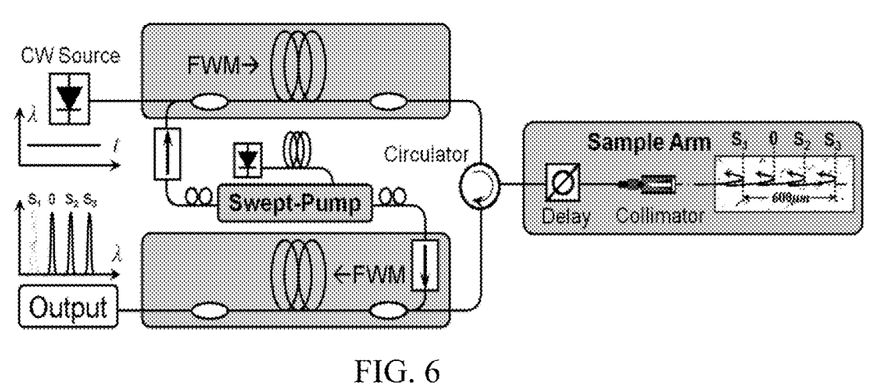
FIG. 6 shows a schematic of an imaging system according to an embodiment of the subject invention.

FIG. 6 shows a schematic diagram of a WET system according to an embodiment of the subject invention. Referring to FIG. 6, a swept pump can be generated from a short pulsed source that may pass through a dispersive fiber. An output signal from the swept pump can be separated into two branches, for example, as the pump for the two-stage FWM, such as FWM1 and FWM2 (of the plots in the lower portion of FIG. 1. In the first-stage FWM, the CW signal having a frequency $f_{cw}$ and the swept pump generate the idler with doubled swept range. The idler can be separated and utilized to illuminate a sample (e.g., a sample under test). Different reflective depths of the sample can give rise to scattering of the idler signal proportional to temporal delay brought about by distances of layers of a sample undergoing imaging.

Figure 7:
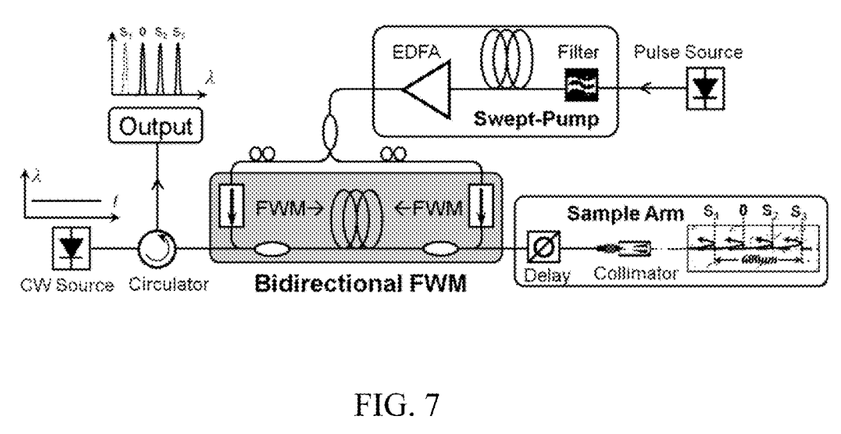
FIG. 7 shows a schematic of an imaging system according to an embodiment of the subject invention.

In certain embodiments, an optical delay line in a sample arm can assist in synchronizing scattered idlers with the second stage pump. Thus, a new idler generated at a frequency $f_{cw}$ can form a signal comprising a spectrum based at least in part on geometrical profiles of features of layers comprising the sample undergoing imaging. In the time-lens system of FIG. 6, a converging and diverging time-lens can be capable of performing in FWM stages, so long as an FWM combines with a signal side and another FWM combines with an idler side. Thus, the two-stage FWM configuration can be simplified to comprise a bidirectional FWM structure, as shown in FIG. 7.

To rapidly capture a signal comprising a spectrum based at least in part on geometrical profiles of features of layers comprising the sample undergoing imaging, similar to the OCT system, a single frame detection may be capable of obtaining depth information of a single illumination point. Thus, referring again to FIG. 5, to capture a 2-dimensional cross-section of an image, for example, a scanning mirror galvanometer (M1) can be used in the sample arm as shown in the left box of FIG. 5.

In FIG. 5(a), which may be used to illustrate a first of two methods, dispersing a spectrum of an output signal from a sample under test onto a spatial CCD sensor can be seen. A second scanning mirror galvanometer (M2) can be utilized, for example, to construct two-dimensional images. Scanning mirror galvanometer M1 and M2 can be synchronized by utilizing a driving signal that may be derived from a single source, for example. In general, the method illustrated in FIG. 5(a) may be simpler and more straightforward than related art approaches, and may consume very few processing resources, or, in some instances, may require no post processing resources. However, the method illustrated in FIG. 5(a) may be limited by a frame rate capacity of the charge coupled device (CCD) sensor, which may be capable of capturing, for example, thousands of frames per second. In contrast, implementations of WET systems can capture millions or billions of frames per second.

Referring again to FIG. 5(b), in a second method, an optical spectrum analyzer, such as a PASTA, can be employed. In one instance, if a PASTA is utilized to synchronize a pump of the WET system, imaging information can be taken at, for example, every frame. By obtaining imaging information with each frame, single-shot and/or single-frame imaging, as shown in FIG. 5(b), can be attained.

According to many embodiments, a WET system can be employed and can be an optical imaging modality capable of capturing tomographic layered images in a non-invasive manner, and enabling ultrafast frame rates with high resolution and sensitivity. In related art techniques, if a continuous wave source is directly reflected from a sample undergoing imaging, it may be difficult to differentiate depth-induced delay of energy scattering from a sample undergoing testing. In many embodiments of the subject invention, a linear frequency shifted device (e.g., a time-lens) can be introduced in front of the sample undergoing imaging. As light or other optical energy transmits forward and backward through the WET system, the spectrum may be stretched and compressed. At the sample site, since illuminating energy may be a swept source, different reflecting depth may result in different output wavelengths after a compression process, thus realizing the separation of different layers. Certain aspects of a WET system may function similarly to those of an OCT technique, which relies on electrical Fourier transformation of the interference fringes.

While there may be little or no interference in the WET process, the device can bring about optical Fourier transform for the optical field, which improves the resolution by a factor of approximately 2 compared with the electrical Fourier transform when using a related art OCT technique. Considering the idler has doubled bandwidth of the pump, it improves the resolution by another factor of approximately 2. Therefore, under the same spectral bandwidth, a WET system can achieve up to 4 times sharper resolution than a related art OCT technique. Since some ultrafast spectro-temporal analyzers based on the time-lens focusing mechanism are available, a WET system can bring about single-shot imaging and provide orders of magnitude improvement in an imaging frame rate, which can be as high as millions or even billions of frames per second.

Advantages of WET versus OCT include, but are not necessarily limited to: (1) no separated reference branch is required in generating the interference pattern (fringes); (2) since the reference branch is not required, the imaging speed is not limited by the mechanical component (such as moving the reference arm in time-domain OCT to generate the fringes); (3) it is a predominantly ultrafast all-optical process, since the output scattered signal directly reflects the spatial information, and no post-processing is required compared with SD-OCT; (4) the WET system can, in principle, achieve four times sharper resolution than the OCT system with the same spectral bandwidth. Therefore, a WET system improves the A-scan rate and the imaging quality, and also largely simplifies system requirement.

All patents, patent applications, provisional applications, and publications referred to or cited herein (including those in the "References" section) are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Figure 4:
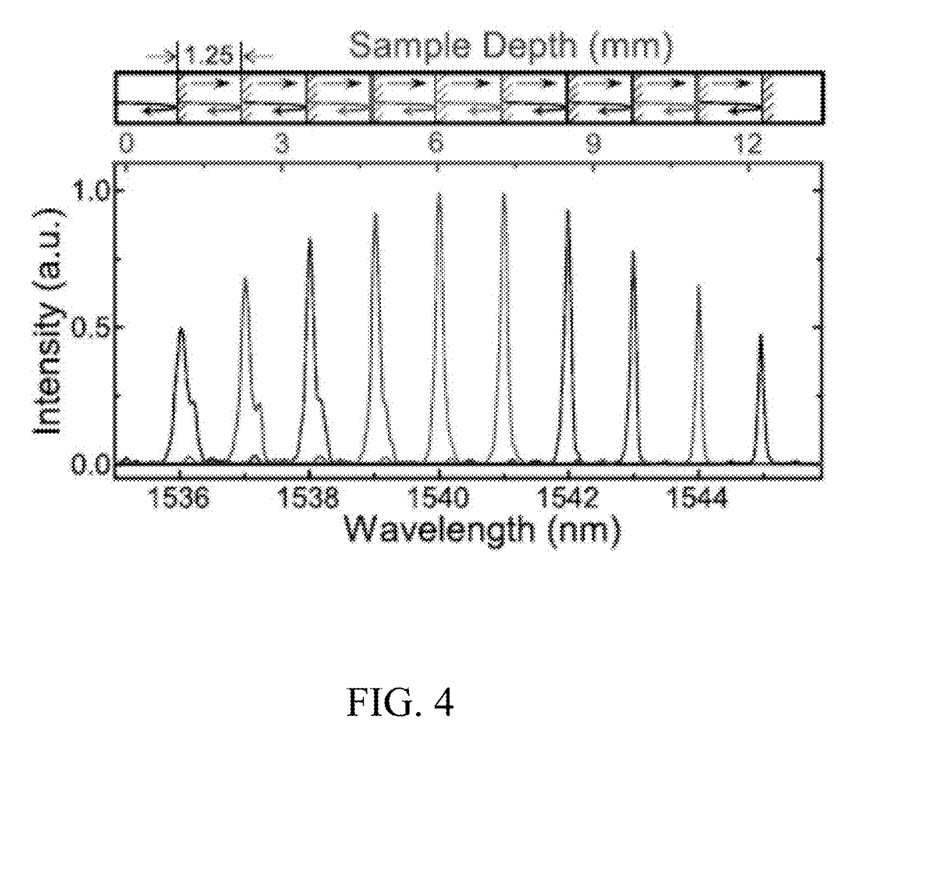
FIG. 4 shows a plot of intensity versus wavelength for characterization of depth-to-wavelength conversion by a system according to an embodiment of the subject invention.

The performance of a WET system as shown in FIG. 2 was evaluated. According to Equation (1), the output wavelength shift ($\Delta\lambda$) is directly proportional to the reflection depth (d). To quantitatively characterize this feature, a precision translation stage was be introduced to control the reflective mirror, which was moved with 1.25-mm separation across 11-mm range, and the results are shown in FIG. 4. It was observed that the 3-dB observation range was up to 1 cm and the depth-to-wavelength mapping ratio was 8=0.8 nm/mm, which matched well with Equation (1). In the WET system, the spatial resolution ($R_{WET}$) refers to the capability of an optical imaging system to distinguish different layers, which can be calculated with the spectral width ($\delta\lambda$) and the mapping ratio ($\epsilon$). The ideal $\delta\lambda$ is determined by the temporal pulsewidth ($\lambda_{BW}DL$), which can be narrowed by the FWM process. It was noted that $\delta\lambda$ can be limited by the high frequency intensity fluctuation of the swept-pump. If there is no intensity fluctuation over the envelope of the swept-pump, and phase-matching condition is satisfied over the whole conversion range, and the spatial resolution of the WET system can be shown as Equation (2).

Based on the experimental pump bandwidth ($\lambda_{BW}$=7.5 nm), the ideal spatial resolution should be 36 μm. Compared with OCT, the WET system can, in principle, achieve four times sharper resolution with the same bandwidth ($\lambda_{BW}$) based on Equation (2). The spectra of these two-stage FWMs are shown in FIG. 3, and it is noted that the idler (I1) bandwidth (10 nm) was not ideally doubled compared to that of the swept-pump (7.5 nm), owing to the higher-order dispersion induced phase mismatch. Therefore, the conversion bandwidth also limited the resolution, and the phase matching condition requires shorter HNL-DSF with lower dispersion coefficient (D) and slope (S). Some advanced dispersion-engineered nonlinear medium, such as a silicon waveguide, helps to achieve 100-nm FWM wavelength conversion bandwidth, which can benefit the implementation of the WET system. The inset of FIG. 3(b) shows the comparison between the input and the output spectra, which was broadened from 0.05 nm (OSA resolution) to $\delta\lambda$=0.12 nm. Two factors contribute to this spectral broadening effect: first, the phase-mismatching decreased the pulsewidth of idler (I1) by 30%, since its bandwidth was degraded from 15 nm to 10 nm after FWM1 (as shown in FIG. 3(a)). Considering the same narrowing effect in FWM2, the pulsewidth of idler (I2) may decrease by half, i.e., broaden the spectral width by a factor of two (from 0.03 nm to 0.06 nm). Second, the temporal intensity fluctuation of the swept-pump introduced another factor of two to the spectral width of the idler (I2) from 0.06 nm to 0.12 nm. According to the measurement in FIG. 4 (based on the OSA with 5-Hz frame rate), the corresponding resolution of the WET system evaluated was $R_{WET}=\delta\lambda/\epsilon$=150 μm, which is less than the ideal case given in Equation (2).

EXAMPLE 2

With ultrafast spectral acquisition modalities, the WET system of Example 1 was compared with a related art OCT system, and the results are shown in Table 1. The systems were compared using the same spectral bandwidth (7.5 nm), and the WET system achieved the same resolution as the OCT system, even with the degradation compared to the ideal case given in Equation (2).

Referring to Table 1, over 100 nm was available as a spectral width for OCT, and it can be an incoherent source in SD-OCT, Fourier domain mode-locking (FDML) laser source, or a semiconductor swept-source with micro-electro-mechanical mirror systems (MEMS) based filter in swept-source OCT. The spectral source in the WET system in this example could have been up to 10 nm, which was limited by the phase-matching condition of the FWM waveguide. The value listed for "Measured R" for the OCT is an estimated value, owing to the small resolution degradation introduced by the OCT system. The A-scan rate of the OCT was limited by the graphics processing unit processing speed (to perform the calibration and Fourier transform) in the SD-OCT.

TABLE 1

Comparison between OCT and WET system under the same spectral width (7.5 nm)

|  | OCT | WET |
| --- | --- | --- |
| Spectral width ($\lambda_{BW}$) | 7.5 mm | 7.5 mm |
| Resolution (R) | $R_{OCT} = 2\ln2\lambda_0^2/(\pi\lambda_{BW})$ | $R_{WET} = \ln2\lambda_0^2/(2\pi\lambda_{BW})$ |
| Theoretic R | 144 μm | 36 μm |
| Measured R | 150 μm | 150 μm |
| Depth range | >1 cm | >1 cm |
| A-scan rate ($f_A$) | 40 kHz | 100 MHz |

The spectral width of the WET system can be narrowed by extending the conversion bandwidth and/or reducing the intensity fluctuation of the swept-pump. Therefore, a more stable swept-pump can lead to a narrower spectral width.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

A. M. Zysk, F. T. Nguyen, A. L. Oldenburg, D. L. Marks, and S. A. Boppart, "Optical coherence tomography: A review of clinical development from bench to bedside," J. Biomed. Opt., 12, 051403 (2007).

D. Huang, E. A. Swanson, C. P. Lin, J. S. Schuman, W. G Stinson, W. Chang, M. R. Hee, T. Flotte, K. Gregory, C. A. Puliafito, and J. G. Fujimoto, "Optical coherence tomography," Science, 254 (5035) 1178-1181 (1991).

S. Yun, G. Tearney, J. de Boer, N. Iftimia, and B. Bouma, "High-speed optical frequency-domain imaging," Opt. Exp., 11, 2953 2963 (2003).

R. A. Leitgeb, W. Drexler, A. Unterhuber, B. Hermann, T. Bajraszewski, T. Le, A. Stingl, and A. F. Fercher, "Ultra-high resolution Fourier domain optical coherence tomography," Opt. Lett., 12, 2156-2158 (2004).

G. N. Hounsfield, "Computerized transverse axial scanning (tomography): Part I. Description of system," Br. J. Radiol 46, 1016-1022 (1973).

R. Damadian, M. Goldsmith, and L. Minkoff, "NMR in Cancer: XVI. FONAR image of the live human body," Physiol. Chem. Phys. 9, 97-100 (1977).

J. J. Wild and J. M. Reid, "Application of echo-ranging techniques to the determination of structure of biological tissues," Science 115, 226-230 (1952).

D. Huang, E. A. Swanson, C. P. Lin, J. S. Schuman, W. G. Stinson, W. Chang, M. R. Hee, T. Flotte, K. Gregory, C. A. Puliafito, and J. G.

Fujimoto, "Optical coherence tomography," Science 254, 1178-1181 (1991). W. Wieser, B. R. Biedermann, T. Klein, C. M. Eigenwillig, and R. Huber, "Multi-Megahertz OCT: High quality 3D imaging at 20 million A-scans and 4.5 GVoxels per second," Opt. Express 18, 14685-14704 (2010).

B. Chance, J. S. Leigh, H. Miyake, D. S. Smiths, S. Nioka, R. Greenfeld, M. Finander, K. Kaufmann, W. Levy, M. Young, P. Cohen, H. Yoshioka, and R. Boretsky, "Comparison of time-resolved and -unresolved measurements of deoxyhemoglobin in brain," Proc. Natl. Acad. Sci. USA 85, 4971-4975 (1988).

M. A. Foster, R. Salem, D. F. Geraghty, A. C. Turner-Foster, M. Lipson, and A. L. Gaeta, "Silicon-chip-based ultrafast optical oscilloscope," Nature 456, 81-84 (2008).

B. H. Kolner, "Space-time duality and the theory of temporal imaging," IEEE J. Quantum Electron. 30, 1951-1963 (1994).

A. E. Conrady, Applied Optics and Optical Design, Part One (Courier Dover Publications, 2011).

C. Zhang, K. K. Y. Cheung, P. C. Chui, K. K. Tsia, and K. K. Y. Wong, "Fiber optical parametric amplifier with high-speed swept pump," IEEE Photonics. Technol. Lett. 23, 1022-1024 (2011).

C. Zhang, P. C. Chui, and K. K. Y. Wong, "Comparison of state-of-art phase modulators and parametric mixers in time-lens applications under different repetition rates," Appl. Opt. 52, 8817-8826 (2013).

M. E. Marhic, Fiber Optical Parametric Amplifiers, Oscillators and Related Devices (Cambridge University Press, Cambridge, 2007).

A. C. Turner-Foster, M. A. Foster, R. Salem, A. L. Gaeta, and M. Lipson, "Frequency conversion over two-thirds of an octave in silicon nano-waveguides," Opt. Express 18, 1904-1908 (2010).

S. Yun, G. Tearney, J. de Boer, N. Iftimia, and B. Bouma, "High-speed optical frequency-domain imaging," Opt. Express 11, 2953-2963 (2003).

R. A. Leitgeb, W. Drexler, A. Unterhuber, B. Hermann, T. Bajraszewski, T. Le, A. Stingl, and A. F. Fercher, "Ultra-high resolution Fourier domain optical coherence tomography," Opt. Lett. 12, 2156-2158 (2004).

D. R. Solli, J. Chou, and B. Jalali, "Amplified wavelength-time transformation for real-time spectroscopy," Nat. Photonics 2, 48-51 (2008).

C. Zhang, J. Xu, P. C. Chui, and K. K. Y. Wong, "Parametric spectro-temporal analyzer (PASTA) for real-time optical spectrum observation," Sci. Rep. 3, 2064 (2013).

T. G. Etoh, C. V. Le, Y. Hashishin, N. Otsuka, K. Takehara, H. Ohtake, T. Hayashida, and H. Maruyama, "Evolution of Ultra-High-Speed CCD Imagers," Plasma Fusion Res. 2, S1021 (2007).

C. Zhang, X. Wei, and K. K. Y. Wong, "Performance of parametric spectro-temporal analyzer (PASTA)," Opt. Express 21, 32111-32122 (2013).

R. Huber, M. Wojtkowski, and J. G. Fujimoto, "Fourier domain mode locking (FDML): A new laser operating regime and applications for optical coherence tomography," Opt. Express 14, 3225-3237 (2006).

What is claimed is:

1. An imaging system, comprising:
   a sample platform;
   a light source to illuminate a sample on the platform;
   a photodetector;
   a linear frequency-shifted device comprising two time-lenses configured to have opposite focal group-dispersion delays from each other and positioned such that light from a sample on the platform Passes through the linear frequency-shifted device before it reaches the photodetector; and
   a processing device in operable communication with the photodetector and configured to receive an output spectrum from the photodetector and realize a spatial-to-wavelength conversion, of the output spectrum, solely in the optical domain.

2. The imaging system according to claim 1, wherein the processing device is an optical spectrum analyzer.

3. The imaging system according to claim 1, wherein the light source comprises a swept-pump, and the imaging system further comprising a first four-wave mixer (FWM) in operable communication with the swept-pump, and a second FWM in operable communication with the swept-pump.

4. The imaging system according to claim 3, wherein the first FWM is a highly-nonlinear dispersion-shifted fiber (HNL-DSF), and wherein the second FWM is an HNL-DSF.

5. The imaging system according to claim 1, wherein the processing device comprises a parametric spectro-temporal analyzer (PASTA).

6. The imaging system according to claim 1, wherein the system is capable of achieving an imaging resolution of 150 µm or less with a spectral width of 7.5 nm.

7. The imaging system according to claim 6, wherein the system is capable of achieving an A-scan rate of at least 100 MHz.

8. A method for imaging a sample, the method comprising:
   placing the sample on a sample platform of an imaging system;
   illuminating the sample with a light source;
   positioning a linear frequency-shifted device that comprises two time-lenses configured to have opposite focal group-dispersion delays from each other such that light from the sample passes through the linear frequency-shifted device before it reaches a photodetector of the imaging system;

receiving, by a processing device in operable communication with the photodetector, an output spectrum from the photodetector; and realizing, by the processing device, a spatial-to-wavelength conversion, of the output spectrum, solely in the optical domain.

9. The method according to claim 8, wherein the processing device is an optical spectrum analyzer.

10. The method according to claim 8, wherein the imaging system further comprises a swept-pump, a first four-wave mixer (FWM) in operable communication with the swept-pump, and a second FWM in operable communication with the swept-pump, and wherein the first FWM provides a signal to the sample platform.

11. The method according to claim 10, wherein the first FWM is a highly-nonlinear dispersion-shifted fiber (HNL-DSF), and wherein the second FWM is an HNL-DSF.

12. The method according to claim 8, wherein the processing device comprises a parametric spectro-temporal analyzer (PASTA).

13. The method according to claim 8, wherein the method achieves an imaging resolution of 150 μm or less with a spectral width of 7.5 nm.

14. The method according to claim 13, wherein the method achieves an A-scan rate of at least 100 MHz.

* * * * *